United States Patent [19]
Sigl

[11] Patent Number: 4,527,990
[45] Date of Patent: Jul. 9, 1985

[54] ELASTICIZED GARMENT AND METHOD FOR ITS MANUFACTURE

[75] Inventor: Wayne C. Sigl, Winnebago County, Wis.

[73] Assignee: Kimberly-Clark Corporation, Neenah, Wis.

[21] Appl. No.: 430,623

[22] Filed: Sep. 30, 1982

[51] Int. Cl.$^3$ .............................................. A61F 13/16
[52] U.S. Cl. ................................................ 604/385 A
[58] Field of Search ............... 604/385, 358, 366, 386, 604/387

[56] References Cited

U.S. PATENT DOCUMENTS

| | | | |
|---|---|---|---|
| 3,639,917 | 2/1972 | Althouse | 2/270 |
| 3,819,401 | 6/1974 | Massengale et al. | 156/85 |
| 3,912,565 | 10/1975 | Koch et al. | 156/85 |
| 4,324,245 | 4/1982 | Mesek et al. | 604/385 |
| 4,337,771 | 7/1982 | Pieniak et al. | 604/385 |
| 4,352,355 | 10/1982 | Mesek et al. | 604/385 |

Primary Examiner—John D. Yasko

[57] ABSTRACT

An elasticized article and a method for elasticizing the article are disclosed in which a strip of elastic material has an end bonded to an end of a strip of shrinkable material to form a single elongated strip having spaced apart opposing ends. The combined strip is bonded at its opposing ends to a flexible substrate of an article with the elastic material in a contracted relaxed condition and the shrinkable means in a stable extended condition. Subsequent to the application of the combined strip to the flexible substrate, the shrinkable means is contracted by shrinking to thereby extend the elastic material and elasticize the flexible substrate.

11 Claims, 9 Drawing Figures

ELASTICIZED GARMENT AND METHOD FOR ITS MANUFACTURE

FIELD OF THE INVENTION

This invention relates to an elasticized article and a method for elasticizing an article. More particularly, the invention relates to a disposable diaper which is elasticized in the waist area and a method for applying elastic in the waist area of the disposable diaper.

BACKGROUND OF THE INVENTION

Articles for uses such as garments or for protective packaging are frequently elasticized to provide a sealed tight fit. Among the various types of garments using elastic means to provide a sealed fit are disposable garments such as disposable diapers which are often sealed in the leg area to prevent leakage of body excretions. There has also been an increased interest in sealing the waist area of disposable diapers for the same purpose.

There are several ways that articles may be elasticized. These include the sewing of elastic into the substrate material which is to form the article, adhering the elastic onto the substrate material, and utilizing a heat shrinkable elastic which is bonded to the article and shrunk by the application of heat to an elastic form which permits the elastic extension and contraction of the substrate. Sewing of elastic into disposable articles is presently seldom used due to its complexity and slowness and resulting high cost. Adhering of the elastic onto a substrate material is commonly used, but nevertheless has its drawbacks. These include the difficulty of handling the elastic in a stretched form, particularly when it is applied in a direction transverse to the direction of movement of a moving substrate material. When elastic is glued to a substrate material in a relaxed condition, it is necessary to first corrugate the substrate material so that it will have excess material which can be extended to stretch the elastic and provide the elasticization effect. The need to corrugate the substrate material also complicates this approach, particularly when the elastic is applied in a direction transverse to the direction of a moving substrate material. Heat shrinkable elastic is applied in a relaxed form and, because it will gather the substrate material with it when it is caused to shrink, it is not necessary that the substrate material first be corrugated. The application of the heat shrinkable elastic in a relaxed form and the elimination of the need to corrugate the substrate material simplifies this approach considerably. However, the temperature level required to shrink the heat shrinkable elastic is above the tolerance level of some substrate materials commonly used in making disposable garments, particularly polypropylene and polyethylene films, and so it is difficult to use heat shrinkable elastic with these substrates. Moreover, heat shrinkable elastics often do not retain a sufficient amount of their elastomeric properties when heated and they thus are frequently unsuitable for many elasticization purposes.

SUMMARY OF THE INVENTION

It is a principal object of this invention to provide an elasticized article and a method for making the elasticized article on a high speed production basis with none of the drawbacks of presently known elasticized articles and methods for their fabrication. It is a more specific object of this invention to provide a method of elasticizing an article in which the elastic can be applied in a relaxed condition without having the substrate material in a corrugated condition. It is a further specific object of this invention to provide an elasticized article in which the elastic material and shrinkable material are separate but connected together and the shrinkable material applies tension to the elastic material.

According to the invention, an elasticized article is provided which includes a flexible substrate, elastic material having a surface area and which is bonded to the substrate over less than the surface area of the elastic material, and shrinkable means having a surface area and which is bonded to the substrate over less than the surface area of the shrinkable means and bonded to the elastic material over a surface area that is less than the surface area of the shrinkable means or the elastic material, the shrinkable means providing a force along a direction between the area of the bond of elastic material to the substrate and the area of the bond of the shrinkable means to the substrate for gathering the substrate upon shrinking whereby, when the substrate is extended, the elastic material applies gathering force to the substrate. The shrinkable material may be responsive to a stimulus such as heat or moisture to shrink to a smaller form such that the elastic material is extended to thereby apply elastic contracting force to the flexible article. Note that the term "elasticized" as used herein means the provision of an elastic contracting force to the article.

DESCRIPTION OF THE DRAWINGS

Further objects and advantages of the invention will appear when taken in conjunction with the accompanying drawings in which.

DETAILED DESCRIPTION OF THE INVENTION

Figure 1:
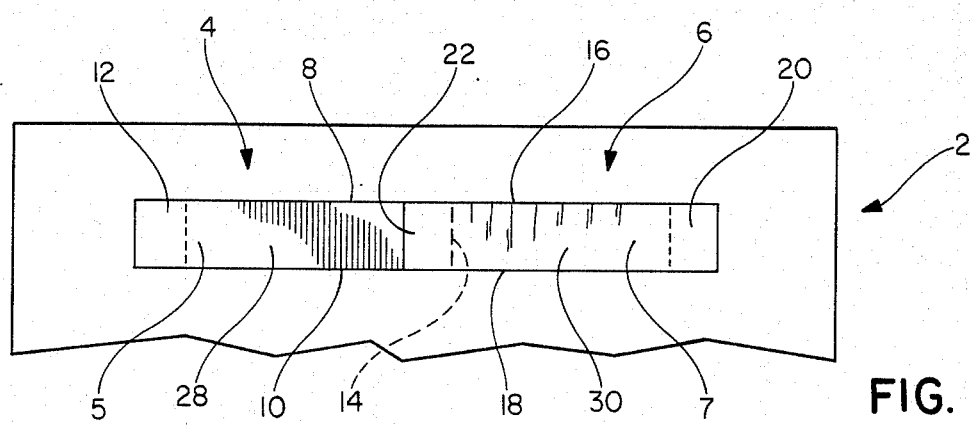
FIG. 1 is a plan view of a portion of an elasticized article according to the invention.

Referring generally to FIGS. 1-4, an elasticized article is shown which includes a flexible substrate 2, an elastic material 4 and shrinkable means 6. The elastic material 4 preferably is in the shape of a strip 5 with a length dimension greater than the width dimension. The elastic material 4 as illustrated in FIGS. 1-4 includes longitudinal edges 8 and 10, opposing ends 12 and 14, a surface area 24 facing the flexible substrate, and a surface area 28 facing away from flexible substrate 2. The shrinkable means 6 comprises a shrinkable material, preferably in the shape of a strip 7 in which the length dimension is greater than the width dimension. The shrinkable means 6 has longitudinal edges 16 and 18, opposite ends 20 and 22, a surface area 26 facing the flexible substrate 2, and a surface area 30 facing away from flexible substrate 2.

A first portion of the surface area 24 of elastic material 4, preferably the end area 12, is bonded to the flexible substrate 2 and a second portion of the surface area 24, preferably the end area 14, is bonded to the surface area 26 of shrinkable means 6, preferably at end area 22. A portion of the surface area 26 of shrinkable means 6, preferably the end area 20, is bonded to the flexible substrate 2. It is important that the elastic material 4 and the shrinkable means 6 are bonded to the substrate 2 at different locations and over surface areas that are less than their entire surface areas to permit the tensioning of the elastic material and the contracting of the shrinkable means without constriction by the substrate and between the bonded locations.

The flexible substrate 2 may comprise a wide variety of materials, depending on the ultimate use of the elasticized article, and will typically be of a material that can be provided in a thin film form. Preferred materials for fabricating disposable diapers are polyethylene film having a maximum thickness of about 5 mils and nonwoven fibrous polypropylene sheeting having a basis weight of from 0.5 to 1.25 oz./yd. The shrinkable means 6 may be of a material which has a stable extended condition, is preferably non-elastomeric, and is responsive to heat to shrink to a relatively stable contracted condition. Suitable materials include heat shrinkable oriented film materials such as ethyl vinyl acetate, polypropylene, polyvinyl chloride, and low density polyethylene. In selecting a heat shrinkable material it is critical that the temperature at which the material shrinks is lower than the heat distortion temperature of the substrate material to which the shrinkable material is bonded. For a polyethylene substrate, the heat distortion temperature is about 250° F.

Figure 2:
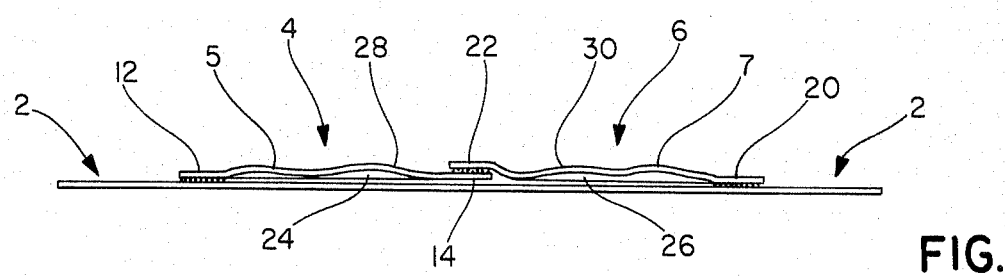
FIG. 2 is an end elevation view of the elasticized article shown in FIG. 1.
Figure 3:
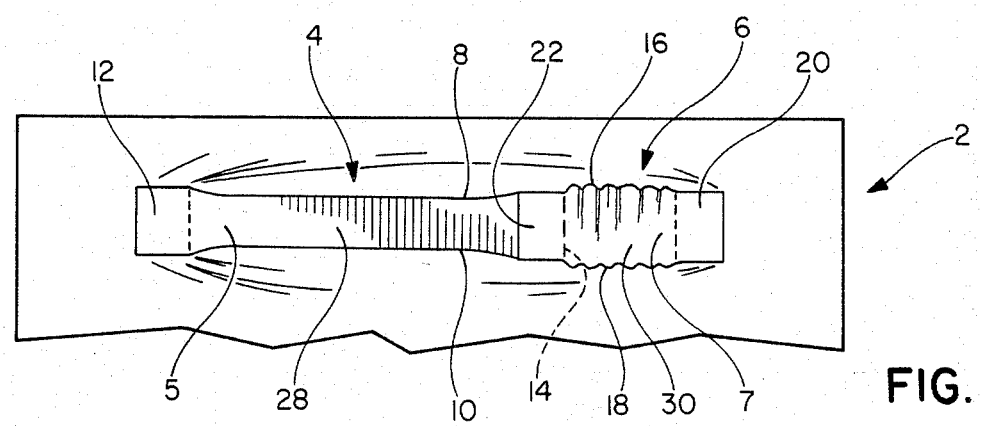
FIG. 3 is a plan view of the elasticized article shown in FIG. 1 with the shrinkable material in a contracted condition and the elastic material in an extended condition.
Figure 4:
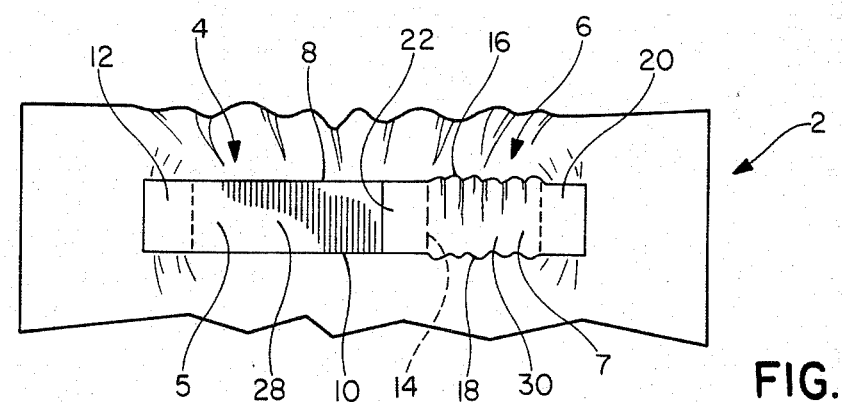
FIG. 4 is a plan view of the elasticized article shown in FIG. 3 with the shrinkable material in a contracted condition, the substrate material gathered, and the elastic material in a relaxed condition.

In the views of FIGS. 1 and 2, the article is shown in a condition in which the flexible substrate 2 is ungathered, the elastic material is 4 is in a relaxed, contracted condition, and the shrinkable means 6 is in a stable, extended condition. In FIG. 3, the flexible substrate 2 is held by means (not shown) in an ungathered condition, the shrinkable means 6 is in a shrunken condition subsequent to its contraction, and the elastic material 4 is in an extended, stretched condition due to the tension applied to it by the contracted shrinkable means 6 while the flexible substrate 2 is held ungathered. Note that the tension force applied by the shrinkable means 6 to the elastic material 4 is along the direction between the location of the bond of the end area 12 of elastic material 4 to the substrate and the location of the bond of the end area 20 of the shrinkable means 6 to the substrate 2. In FIG. 4, the shrinkable means 6 is shown in its contracted condition and the elastic material 4 is in a relaxed, contracted condition. The flexible substrate 2 is in a gathered condition due to the contracting force applied to it by the elastic material 4 through the bonded end area 12 of the elastic material 4 and the bonded end area 20 of the shrinkable means 6.

Figure 9:
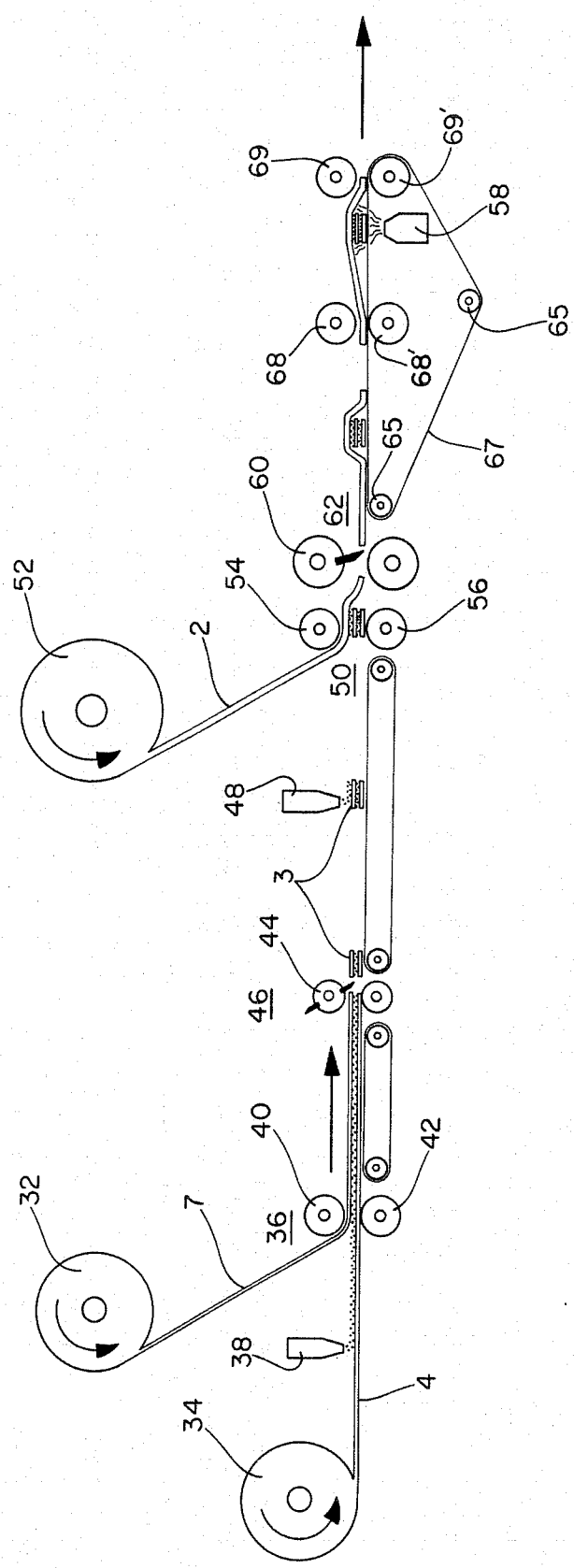
FIG. 9 is a schematic side elevation view of apparatus for elasticizing an article according to the invention.

The elasticized article may be made, as illustrated in FIG. 9, by feeding a roll 32 of continuous shrinkable material and a roll 34 of continuous elastic material 4 to a combining station 36 with the elastic material 4 in a relatively relaxed condition and applying adhesive to the elastic material 4 with an adhesive applicator means 38. The rolls 32 and 34 are positioned such that the shrinkable material and elastic material are overlapped only along one longitudinal edge of each material at the combining station 36. The adhesive is applied to either the elastic material or the shrinkable material in the overlapped area. The overlapped area is then passed between nip rolls 40 and 42 to bond the shrinkable material and elastic material together along the overlapped margins. The combined shrinkable material and elastic material 4 is then severed by cutting means 44 at cutting station 46. The severed strips of combined shrinkable material strips 7 and elastic material strips 5 each have adhesive applied to their respective end areas 12 and 20 by adhesive applicator means 48 and the combined strips are then moved on to an application station 50 where they engage a continuous web of flexible substrate 2. The flexible substrate 2 is supplied from a roll 52 on to a continuous moving screen 67 which moves continuously around rolls 69' and 65. The strips of combined elastic material 4 and shrinkable material are passed between nip rolls 54 and 56 to bond the end areas 12 and 20 of the elastic material 4 and shrinkable material 6, respectively, to the substrate 2. The web of flexible substrate material 2 may then be severed by cutting means 60 at cutting station 62 into a series of separate web pieces. The shrinkable material 6 may then be subjected to a stimulus, such as heat from a heat source 58, to elevate its temperature and cause it to shrink to a contracted condition and provide elasticized articles according to the invention. However, due to the clamping of the web of flexible substrate 2 by clamping rolls 68, 68' and 69, 69', the web maintains its width and the elastic material strip 5 assumes an extended, tensioned condition as shown in FIG. 3.

An alternative embodiment of the invention is illustrated in FIGS. 5-8 in which the elasticized article is a disposable diaper. Those elements shown in FIGS. 5-8 which are the same as or similar to corresponding elements in the embodiment of FIGS. 1-4 are identified with the same numerals and only those elements in FIGS. 5-8 which are substantially different from or in addition to the elements of FIGS. 1-4 are identified with different numerals. The disposable diaper comprises a flexible substrate in the form of a liquid impervious cover sheet 70, a flexible substrate in the form of a liquid pervious body side liner sheet 72 which is joined to the sheet 70 along the periphery of the two sheets, and an absorbent pad 74 disposed between the sheets 70 and 72. The diaper has a front waist area 64 and a rear waist area 66. The diaper also includes elastic strips 76 and 78 located in the leg area of the diaper for sealing the diaper about the legs when the diaper is being worn, and waist fastening tapes 80 and 82 for securing the diaper around the waist when the diaper is being worn.

Figure 5:
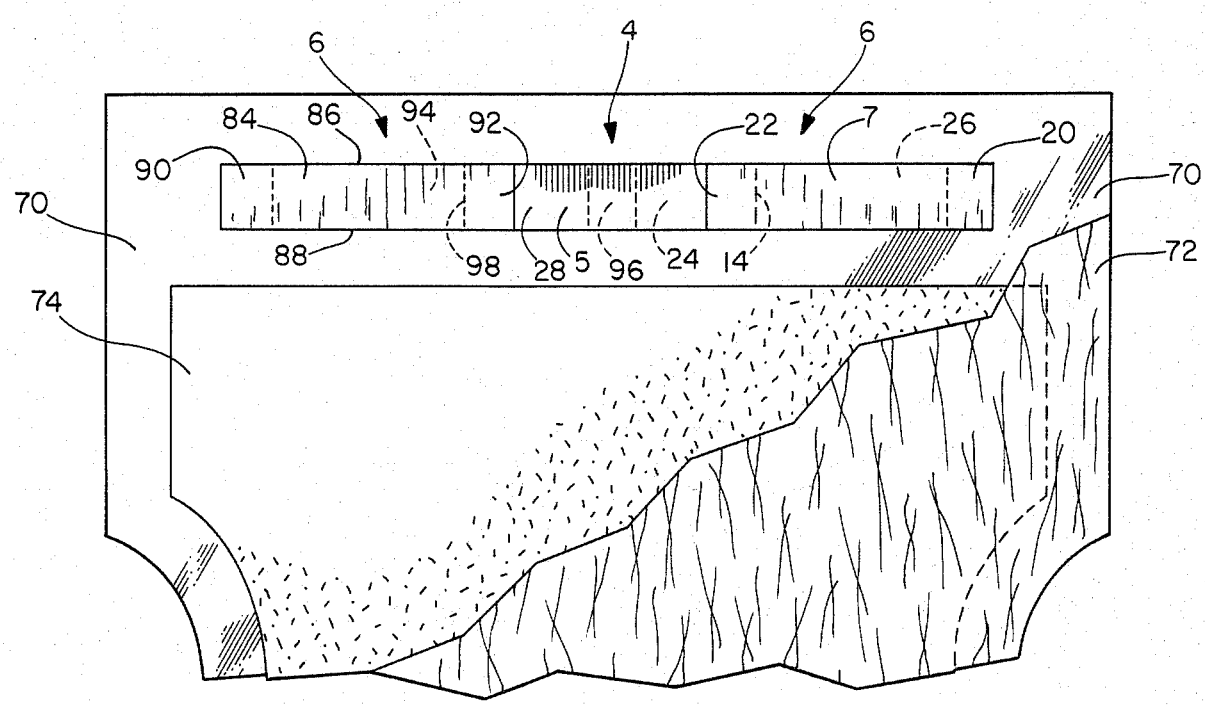
FIG. 5 is a plan view, partially broken away, of an alternative embodiment of the invention in which the elasticized article is a disposable diaper.
Figure 6:
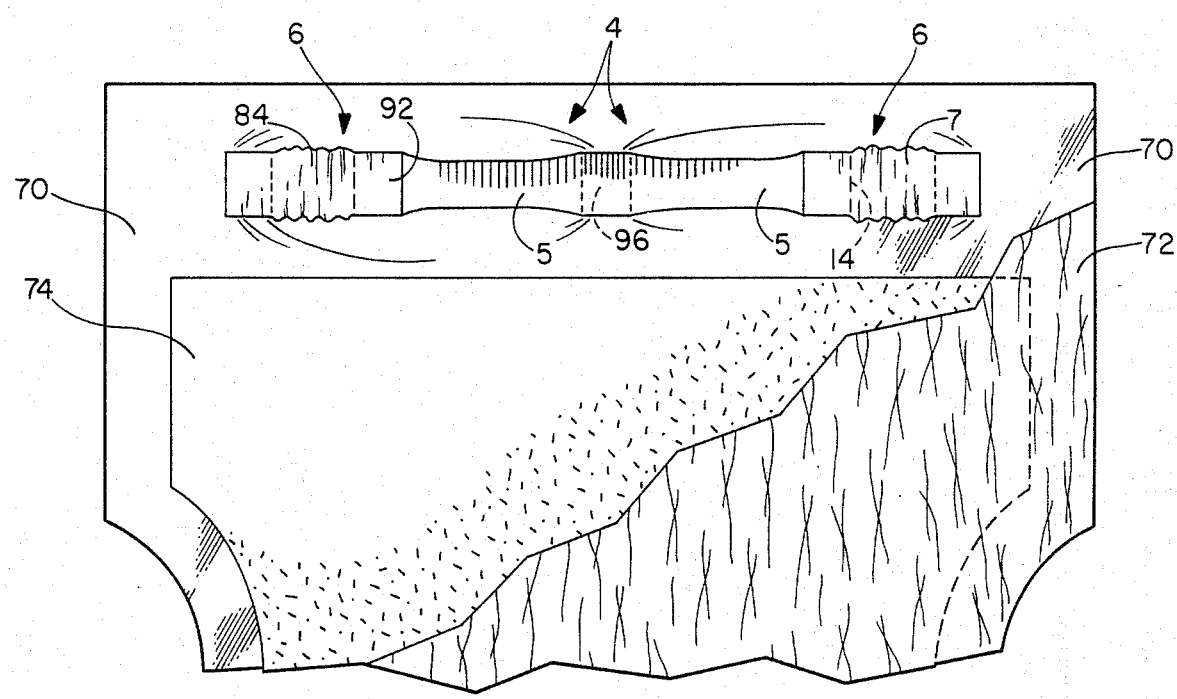
FIG. 6 is a plan view, partially broken away, of the elasticized disposable diaper of FIG. 5 with the shrinkable material in a contracted condition and the elastic material in an extended condition.

As is best illustrated in FIGS. 5 and 6, the shrinkable means 6 includes a shrinkable material strip 7 and a shrinkable material strip 84 having opposite end areas 90 and 92 and surface area 94 facing the cover sheet 70. The elastic material 4 includes elastic strip 5 having opposite end areas 14 and 98 on the surface area 28 facing away from the sheet 70. The strip 5 also has a surface area 24 facing the sheet 70. A portion of the surface area 94 of shrinkable strip 84, preferably the end area 90, is bonded to the cover sheet 70 and a portion of the surface area 94, preferably the end area 92, is bonded to a portion of the surface area 28, preferably end area 98, of elastic strip 5. A portion of the surface area 26 of shrinkable strip 7, preferably the end area 20, is bonded to the cover sheet 70 and a portion of the surface area 26, preferably the end area 22, is bonded to a portion of the surface area 28, preferably end area 14, of elastic strip 5. The elastic strip 5 has a portion 96 of its surface area 24 intermediate its end areas 98 and 14 bonded to the cover sheet 70.

Figure 7:
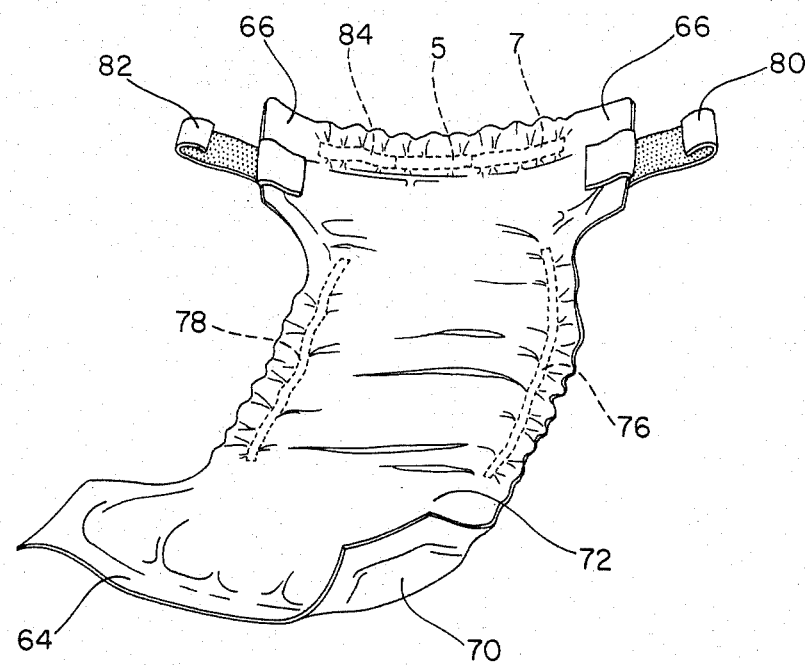
FIG. 7 is a simplified perspective view of the elasticized disposable diaper illustrated in FIGS. 5 and 6, just prior to the fitting of the diaper onto an infant, with an elasticized waist area in a relaxed condition.
Figure 8:
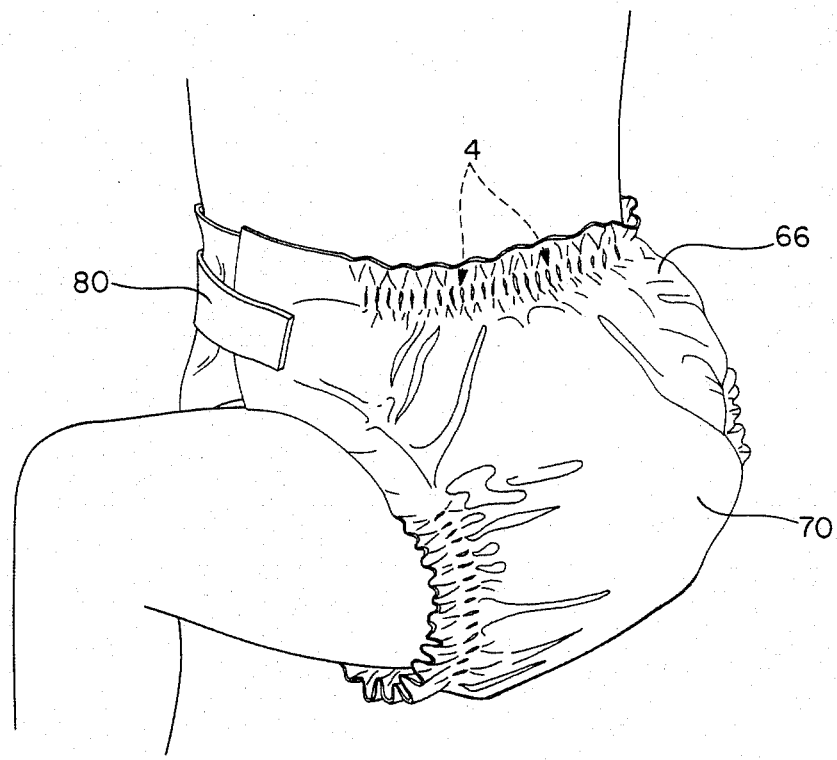
FIG. 8 is a perspective view showing the diaper of FIG. 7 being worn by an infant.

The disposable diaper is illustrated in FIG. 5 with the cover sheet 70 in an extended, ungathered condition, the elastic material strip 5 in a relaxed, contracted condition, and the shrinkable material strips 7 and 84 in a stable, extended condition. In FIG. 6, the cover sheet 70 is in an extended, ungathered condition, the material strips 7 and 84 are in a contracted condition, and the elastic material 4 is in a tensioned, extended condition. Due to the bonding of the elastic material strip 5 at the intermediate area 96, the tension applied to the strip 5 by the shrinkable material strip 7 is between the bonded area 96 and the end area 14 and the tension applied by the strip material 84 is between the bonded area 96 and the end area 92. Where the bonded surface portion 96 is located equidistant between its end areas 92 and 14, the tension applied to the elastic strip 5 will be asymetrical about the bonded area 96. In FIG. 7, the diaper is shown in a condition in which cover sheet 70 and the liner sheet 72 attached to it are in a contracted condition, the shrinkable material strips 7 and 84 are in a contracted condition, and the elastic strip 5 is in a contracted, relaxed condition. In FIG. 8, illustrating the diaper being worn by an infant, the waist tapes 80 and 82 have been attached about the waist of the diaper to tension and extend the elastic material 4 so that it is in a condition similar to that shown in FIG. 6 and the tension of the elastic causes a tight seal between the skin of the infant and the liner sheet 72 of the diaper.

It will be understood that the foregoing description of the present invention is for purposes of illustration only and that the invention is susceptible of a number of modifications or changes, none of which entail any departure from the spirit and scope of the present invention as defined in the hereto appended claims.

What is claimed is:

1. An article comprising a flexible substrate, elastic material having a surface area and being bonded to the substrate over a portion of the surface area of the elastic material, and shrinkable means having a surface area and being bonded to the substrate over a portion of the surface area of the shrinkable means and bonded to the elastic material over another portion of the surface of the shrinkable means that is less than the surface area of the elastic material, the shrinkable means providing a force along a direction between the area of the bond of the elastic material to the substrate and the area of the bond of the shrinkable means to the substrate for gathering the substrate upon shrinking whereby, when the substrate is extended, the elastic material applies gathering force to the substrate.

2. The article according to claim 1 wherein, prior to shrinking of the shrinkable means, the flexible substrate, elastic material and shrinkable means respectively have an ungathered condition, an unextended condition, and a stable extended condition, and, subsequent to shrinking of the shrinkable means, the flexible substrate, elastic material and shrinkable means respectively have a gathered condition, an unextended condition, and a contracted condition.

3. The article according to claim 1 or 2 wherein:
the elastic material comprises a strip having first and second opposing ends, the first end being bonded to the substrate; and
the shrinkable means comprises a strip of shrinkable material having opposing ends, one of the ends of the shrinkable material being bonded to the substrate and the other of the ends of the shrinkable material being bonded to the second end of the elastic material.

4. The article according to claims 1 or 2 wherein:
the elastic material comprises a strip having first and second ends and being bonded to the substrate intermediate the ends; and
the shrinkable means comprises a pair of strips of shrinkable means each having third and fourth ends, the third end of each of the pair of strips being respectively bonded to the first and second ends of the elastic material and the fourth ends being bonded to the substrate.

5. The article according to claims 1 or 2 wherein the shrinkable means comprises a shrinkable film having a thickness not greater than 5 mils.

6. The article according to claim 1 wherein the shrinkable means comprises a material which shrinks in response to elevation of its temperature.

7. An article comprising a flexible substrate, an elastic material in an unextended condition and having an area bonded to the substrate, and a shrinkable material in an extended condition, said shrinkable material having a first area spaced from said area of the elastic material and bonded to the substrate and a second area located intermediate and spaced from the first area and the bonded area of the elastic material and bonded to the elastic material whereby, after the shrinkable material is caused to shrink, the elastic material and shrinkable material together gather the substrate and the elastic material applies elastic contracting force to the substrate when the latter is extended.

8. The article according to claim 7 wherein;
the article comprises a garment;
the flexible substrate is a material conforming at least in part to the body of the wearer of the garment;
the elastic material in an extended condition while the garment is being worn; and
the garment and the body of the wearer have a sealed condition between the body and the extended elastic material.

9. The article according to claim 8 wherein the garment comprises a disposable diaper.

10. The article according to claim 9 wherein
the disposable diaper has a waist area; and
elastic material and shrinkable material together have a length and the length is positioned in the waist area transversely of the length of the diaper.

11. In a disposable diaper having a liquid impervious cover sheet, a liquid pervious body side liner sheet positioned opposite the cover sheet, and joined to the cover sheet along the peripheries of the two sheets and an absorbent pad disposed between the cover and liner sheets, a crotch area intermediate the ends of the diaper, a waist area at each end of the diaper, elastic means comprising:

a strip of elastic material having first and second ends, a strip of heat shrinkable material having third and fourth ends, the first and fourth ends being bonded to at least one of the cover and linear sheets in the waist area, the second end being bonded to the third end, the elasticization means being disposed transversely of the length of the diaper, the heat shrinkable material having a stable extended condition prior to shrinking and a contracted condition subsequent to shrinking, the elastic material having a relaxed, contracted condition when the heat shrinkable material is in its extended condition and an extended condition while the diaper is being worn and the heat shrinkable material is in its contracted condition.

* * * * *